United States Patent [19]
Smart

[11] Patent Number: 5,449,919
[45] Date of Patent: Sep. 12, 1995

[54] BORESCOPE DRILL PIPE AND LIGHT GUIDE SLEEVE

[75] Inventor: Ken Smart, Toronto, Canada

[73] Assignee: The Carsen Group Inc., Markham, Canada

[21] Appl. No.: 193,469

[22] Filed: Feb. 8, 1994

[51] Int. Cl.$^6$ ............................................. G01N 21/64
[52] U.S. Cl. ............................ 250/461.1; 250/458.1; 356/241
[58] Field of Search ............... 356/241; 250/227.26, 250/458.1, 461.1

[56] References Cited

U.S. PATENT DOCUMENTS

| | | | |
|---|---|---|---|
| 3,294,085 | 12/1966 | Wallace. | |
| 4,241,729 | 12/1980 | Aoshiro | 356/241 |
| 4,273,110 | 6/1981 | Groux | 128/6 |
| 4,657,387 | 4/1987 | Heising | 356/241 |
| 4,732,474 | 3/1988 | Chikama | 356/241 |
| 4,967,092 | 10/1990 | Fraignier | 356/241 |
| 5,088,819 | 2/1992 | Storz | 356/241 |
| 5,133,035 | 7/1992 | Hicks | 385/117 |
| 5,202,758 | 4/1993 | Tamburrino | 250/461.1 |

*Primary Examiner*—Carolyn E. Fields
*Attorney, Agent, or Firm*—Jane Parsons

[57] ABSTRACT

A borescope for inspecting the inside of bores such as drill pipe bores includes an elongate shaft to extend into the pipe. The shaft has an optical eye for directing incident light from a light source toward an inside surface of the bore and a receptor to receive emitted light therefrom. The shaft may be rotated eccentrically about the bore axis so that the distance of the optical eye from a sector of the interior surface to be inspected is always less than the radius of the bore.

10 Claims, 4 Drawing Sheets

BORESCOPE DRILL PIPE AND LIGHT GUIDE SLEEVE

BACKGROUND OF THE INVENTION

1. Field of the Invention

This invention relates to apparatus for inspecting the interior wall of a pipe or bore. Such apparatus is frequently referred to as "a borescope" and will be referred to as such herein.

2. Acknowledgement of Prior Art

Borescopes are used for inspection of the interior surface of all types of bore such as bore holes for wells or for mining or the interior bores of pipes. They generally utilize the principle of directing light towards an inner reflecting surface of a bore to be inspected, and monitoring reflected light therefrom. Examples of borescopes utilizing this principle are disclosed in U.S. Pat. No. 4,732,474 to Chikama issued Mar. 22, 1988 and in U.S. Pat. No. 5,088,819 to Storz issued Feb. 18, 1992, U.S. Pat. No. 4,967,092 to Fraignier et al issued Oct. 30, 1990 and in U.S. Pat. No. 4,657,387 to Heising et al issued Apr. 14, 1987. The general principle is also utilized in apparatus for inspecting any reflecting surface. Thus endoscopes for surgically inspecting interior parts of the body cavity of humans and animals may utilize this principle as, for instance, in the endoscopes of U.S. Pat. Nos. 4,241,729 and 3,294,085.

Known borescopes may comprise an optical probe located at the distal end region of an elongate rod or sleeve which is capable of being projected into the bore to be inspected. The probe may be connected to a monitor at the proximal end of the rod or sleeve outside the bore. Light from the probe is directed towards the wall of the bore and reflected light signals are transmitted to the monitor. The longitudinal position of the probe within the bore may be adjustable.

Borescopes of the type just described vary in their efficiency dependent on the radius of the bore whose wall is to be inspected. If the bore is of small radius the path travelled from the optical source to the bore wall and back to the receptor is small and loss of brightness and effect of optical aberrations may be minimal. On the other hand, if the radius of the bore is large the path travelled from the optical source, to the bore wall and back to the receptor is large and appreciable distortions may occur. Moreover, lack of definition may also become a problem.

Considerable effort has been put into the design of optical probes small enough to be used in narrow bores (Heising), or for all round viewing (Fraignier), or for the provision of flexible shafts to extend round pipe or bore bends (Storz).

Optical technology for the inspection of a surface within a pipe or bore and at a considerable distance away from the monitor has become very sophisticated as may be seen from Heising et al and Fraignier et al in respective U.S. Pat. Nos. 4,657,387 and 4,967,092 referred to above. The sophisticated apparatus which is now available may allow for detailed inspection of sectors of inner pipe wall. If, due to the geometry of the pipe and a probe which is rotatable coaxially therein is such that close inspection of the pipe wall is not possible, much of the advantage of the modern technology may be lost. The present inventor has addressed this problem.

SUMMARY OF THE INVENTION

According to the invention there is provided apparatus for inspecting an interior surface of a straight bore, for example, the bore of a drill pipe, comprising: mounting means to attach the apparatus to a mouth of the bore; a rigid shaft locatable in the bore parallel to the bore axis and offset therefrom to project a first shaft end out of the bore; light means attached to a second end of the shaft and comprising an emitter to emit an incident light beam and a receiver to receive a light beam; the light means being arranged to respectively direct incident light towards a sector of the interior surface of the bore and receive emitted light therefrom; a monitor; a light source; incident light transmission means extending along the length of the shaft to transmit light from the light source to the emitter; emitted light transmission means extending along the length of the shaft to transmit light from the receiver to the monitor; and means to move the shaft eccentrically about the bore axis.

In most cases, the bore which may be either a pipe bore or a mine shaft bore such as a well bore, will be cylindrical. Moreover, the bore will usually be oriented in a horizontal orientation, although it may be vertical. Generally the apparatus will be used for inspecting the inside straight pipes such as drill pipes in the regions such as welds, joins between pipe sections, or regions where damage is suspected.

The apparatus may allow incident light to be projected towards the pipe wall over a distance appreciably less than the radius of the pipe. Similarly emitted light travels from the pipe wall to the receptor over a distance less than the radius of the pipe. As the shaft moves eccentrically about the axis of the pipe the distance travelled by incident and emitted light remains constant.

The shaft may be a sleeve and the incident light transmission means and the emitted light transmission means are located inside the sleeve. Conveniently the light source may be a source of ultraviolet light and the incident light transmission means and the emitted light transmission means are optical fibres.

Due to the fact that the light means is located near the pipe wall it may be possible to inspect sectors of the pipe wall with a greater degree of accuracy than if it were located at the axis of the pipe.

Of course it is desirable that the light means is longitudinally adjustable within the bore. This involves providing means to longitudinally adjust the position of the shaft within the pipe. Preferably the shaft is longitudinally adjustable in indexed increments.

In one embodiment, the mounting means comprises a platform attachable to a mouth of the bore either by internal threading or by external threading to align the shaft parallel with axis of the bore and the means to eccentrically move the shaft about the bore axis is an eccentric mounted on the platform to be rotatable about an axis coaxial with the bore axis and having an eccentric bearing therethrough, the shaft extending through the bearing for movement therewith on rotation of the eccentric.

The eccentric may comprise a disc arranged parallel and concentric with the platform and rotatable about its axis, the eccentric bearing for the shaft being offset from said axis, and a circular strap geared to gearing around the rim of the disc to rotate the disc. The circular strap may be driven manually or through a motor. When it is driven manually it may be provided with a handle.

A spacer may be provided to space the platform axially from the mouth of the bore, and the platform is attached to the mouth of the bore through the space. The spacer may comprise a screw threaded bore to engage a complementary externally screw threaded spigot of the mouth of the bore.

BRIEF DESCRIPTION OF THE DRAWINGS

An embodiment of the invention will now be described by way of example with reference to the drawings in which.

DETAILED DESCRIPTION OF A PREFERRED EMBODIMENT

The drawings show an embodiment of apparatus according to the invention for inspecting the inner wall of a vertical drill pipe 10.

It should, of course, to be understood that the apparatus may be used to inspect the interior of any bore provided that means are provided at the mouth of the bore for secure mounting of the apparatus.

Figure 1:
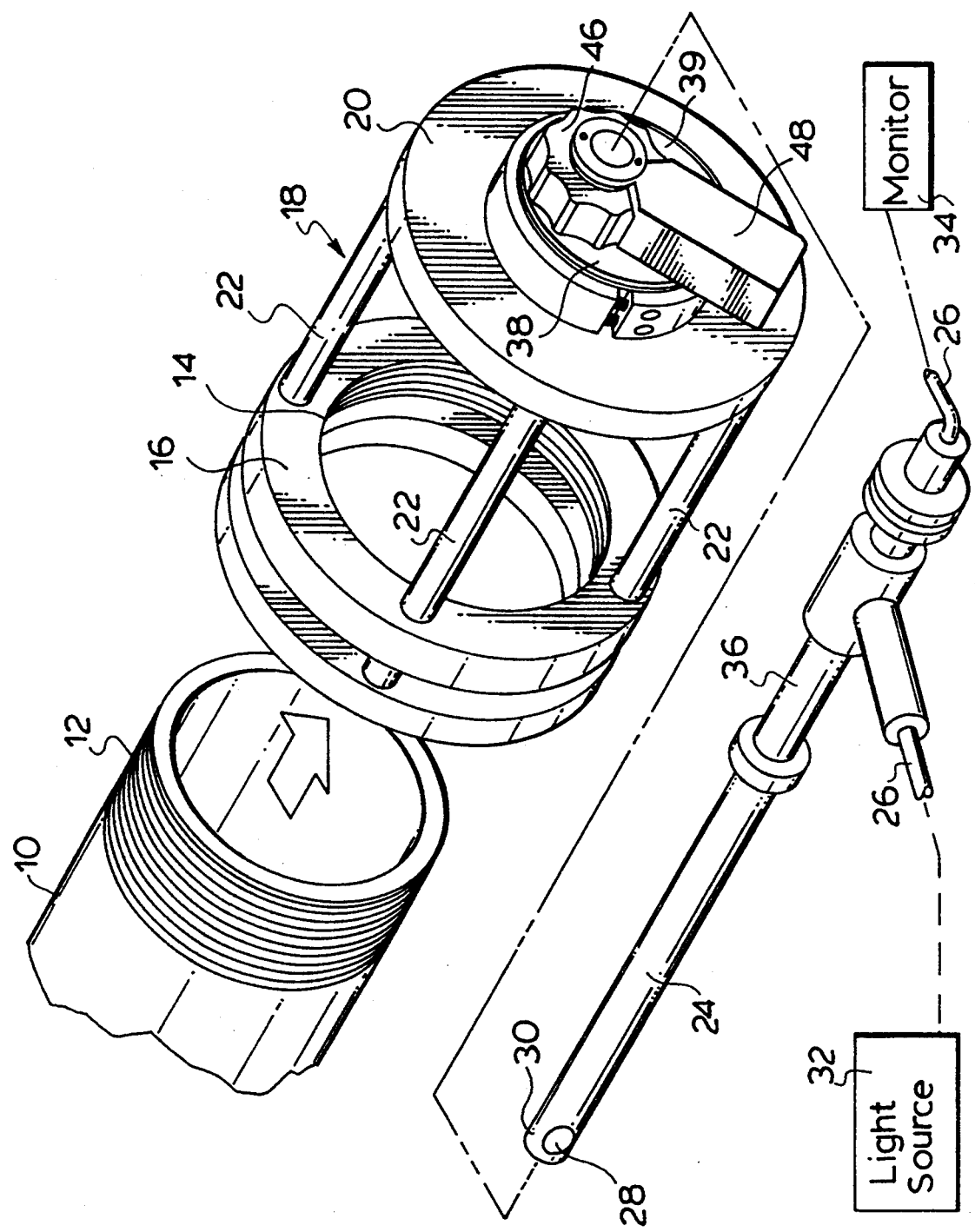
FIG. 1 is a view of one embodiment of apparatus according to the invention having mounting means for mounting it on a drill pipe having external threading.
Figure 2:
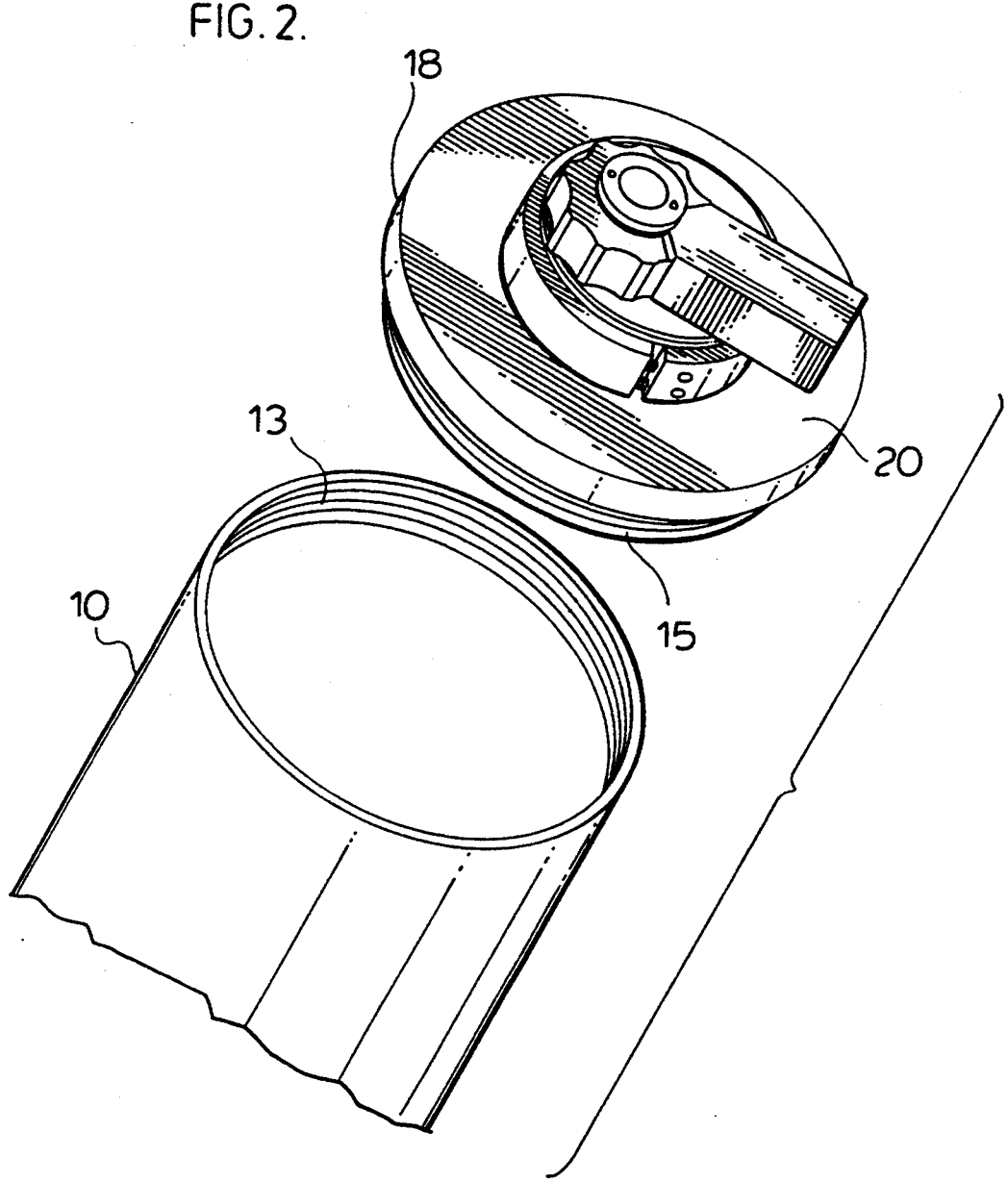
FIG. 2 is a perspective view of apparatus similar to that of FIG. 1 but having means for mounting on a drill pipe having internal threading.
Figure 3:
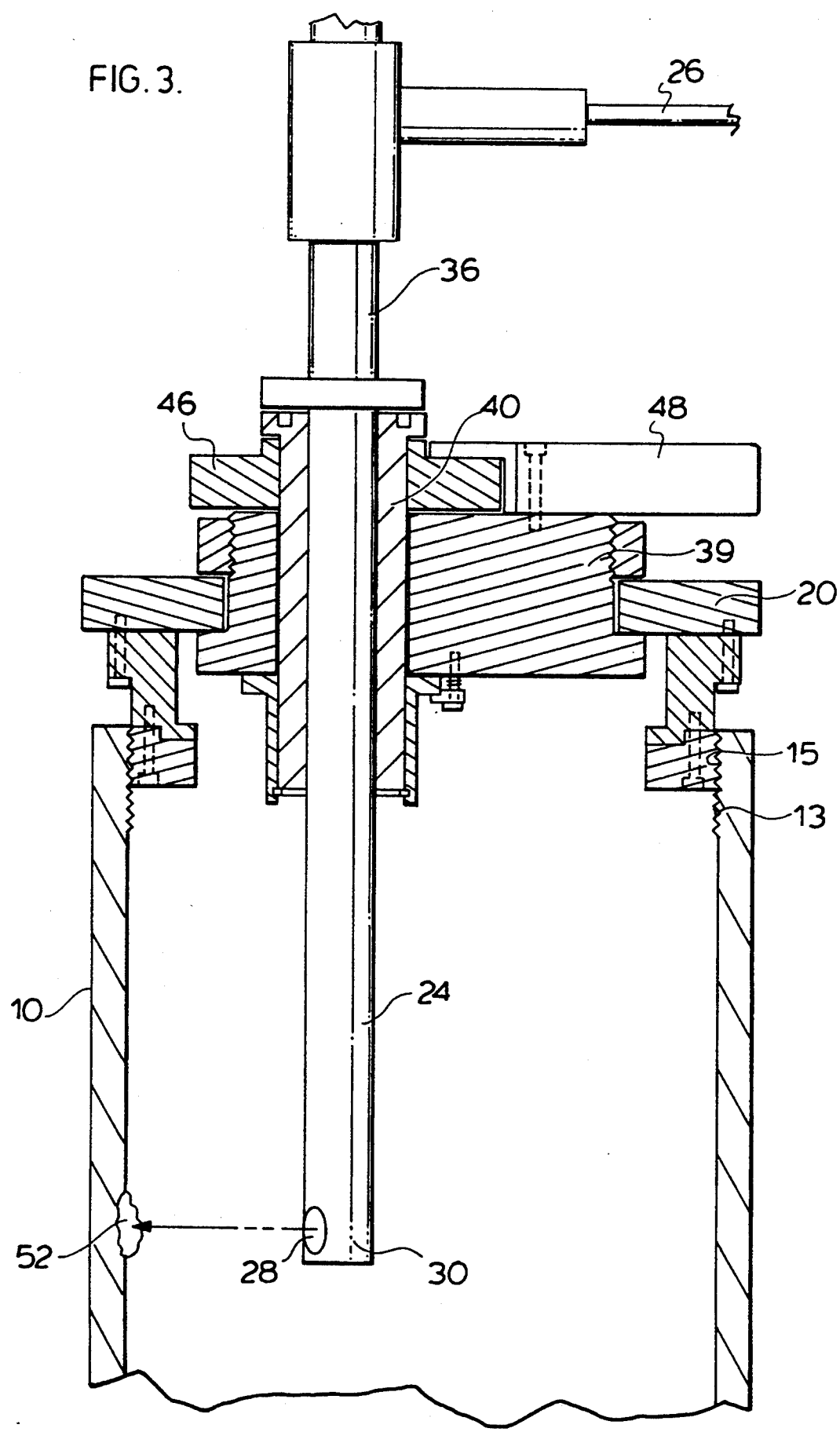
FIG. 3 is a central longitudinal section of the apparatus of FIG. 1.
Figure 4:
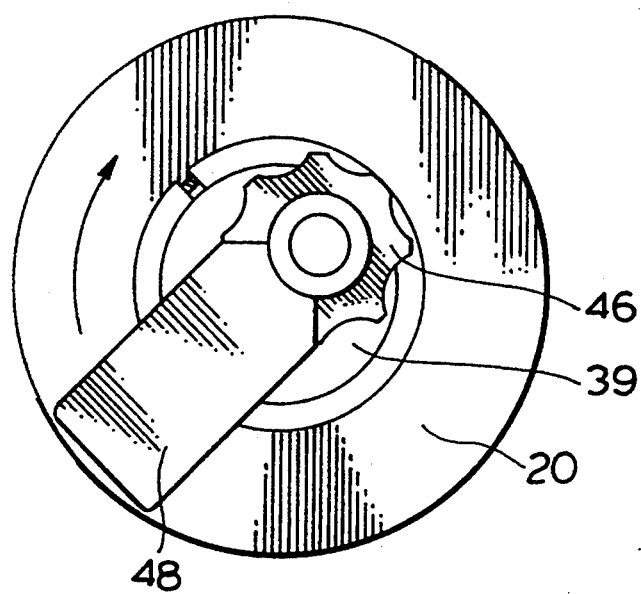
FIG. 4 is a view of the apparatus of FIG. 2 as viewed from the top.
Figure 5:
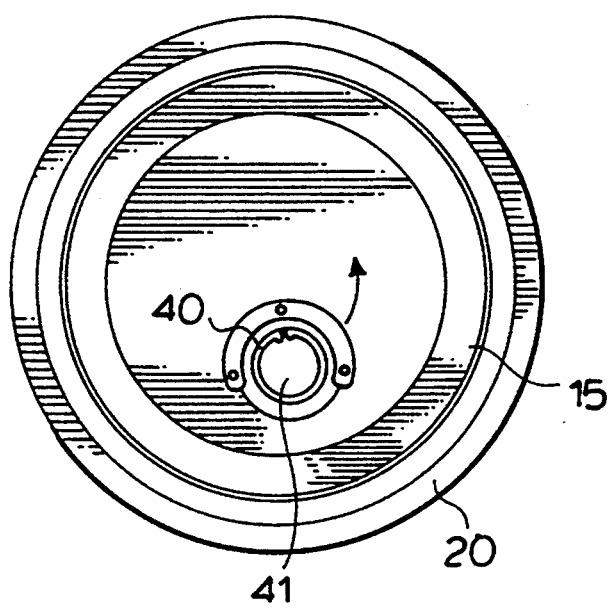
FIG. 5 is an underside view of a further embodiment of the invention.

The drill pipe 10 may have any orientation, i.e. it may be vertical or horizontal or angled. In fact in practice it is quite likely that it will be horizontal. Any orientation shown in the drawings is for ease of illustration. In the embodiment shown in FIGS. 1 and 3 the drill pipe 10 is provided with an externally screw threaded spigot 12 which is engageable with a screw threaded socket 14 of an annular plate 16 of mount 18. In the embodiment shown in FIGS. 2, 4, and 5 the drill pipe 10 is provided with an internally threaded socket 13 which is engageable with a screw threaded spigot 15 of platform 20 of mount 18.

When the apparatus is to be mounted on an externally threaded drill pipe, the mount 18 comprises a platform 20 spaced above plate 16 by four spacing pedestals 22 of which only three can be seen. Thus, it is possible to screw plate 16 onto the upper end 12 of the drill pipe so that the spigot 12 of the drill pipe extends into the space between plate 16 and annular platform 20 and thus does not foul operating parts above it. On the other hand, when the apparatus is to be mounted on an internally threaded pipe, the mount 18 comprises only annular platform 20.

A shaft 24 extends into the drill pipe 10 through the spigot 12, the plate 16 and platform 20 of mounting 18. The shaft 24 comprises a sleeve carrying light transmission connectors 26 between an optical eye 28 at a lower end 30 of the shaft 24, and on the one hand, and a light source 32 and, on the other hand a monitor 34. The optical eye 28 is attached to the end 30 of shaft 24 to direct a beam incident light towards a sector of the interior surface of drill pipe 10 generally normal to the surface. Suitably the light is ultraviolet light (although white light can be used) which, when directed at the internal surface of a pipe which has been treated with a fluorescent dye or magnetic fluorescent particles, causes fluorescence when the dye concentrates e.g. in flaws or defects. This may provide a very clear visual image. It is, however, important that the optical eye is a set distance from the surface to be inspected. The eye is located to receive emitted light from the interior wall of drill pipe 10. The connections 26, which may be a liquid optic system or optical fibres, carry incident light from the optical source 32 to the optical eye and carry emitted light from the optical eye to the monitor 34 which may be an eyepiece or camera.

The shaft 24 is located within the drill pipe 10 to project from it as end portion 36 and is located parallel but not coaxial with the longitudinal axis of the drill pipe 10 by means of an eccentric 38.

Eccentric 38 comprises a disc 39 rotatable on bushing 40 and having an offset bearing aperture 41 through which shaft 24 passes. Bushing 40 holds the shaft 24 of the borescope and is tightenable by means of compression ring 46. Thus disc 39 is able to rotate coaxially about the axis of drill pipe 10 so that bearing aperture 41 describes a circle about the axis of drill pipe 10. When shaft 24 of disc 39 is located in bushing 40 of disc 39 and disc 39 is rotated, then the shaft 24 moves eccentrically about the axis of drill pipe 10. Thus, optical eye 28 on lower end 30 of shaft 24 will describe a circle around the axis of drill pipe 10. Optical eye 28 is arranged to direct incident light generally radially outwardly towards the inner wall of drill pipe 10.

Due to the arrangement of shaft 24 in bushing 40 of disc 39, the distance of optical eye 28 from the wall of the pipe 10 will always be less than the radius of drill pipe 30. The actual distance of optical eye 28 from the interior wall of drill pipe 30 will depend on the actual location of bushing 40 disc 39. It is quite possible that disc 39 be provided with more than one aperture so that the distance of bushing 40 from the centre of disc 39 may be varied to vary the distance of the optical eye from the inner wall of the drill pipe may be varied. A disc having a plurality of bearing apertures 41 at different distances from the axis may be useful if the apparatus is to be used to inspect the interior walls of drill pipes of different radii. When it is desired to use the apparatus or drill pipes of different radii, it is only necessary to provide different threaded socket 14 or threaded spigot 13.

While the operation of the eccentric 38 may be by any conventional means, it may be convenient to provide a handle 48 to turn disc 39.

It is important that optical eye 28 always be directed towards the interior wall of the drill pipe 10. Thus, it is important that shaft 24 should not rotate about its own axis to allow the optical eye 28 to be directed in other directions, for example, diametrically opposite to the direction indicated in the drawings. For this reason, the shaft 24 may be secured in a fixed bushing 40 of eccentric 38 but should be freely rotatable in compression ring 46.

The optical eye itself may utilize any convenient technology but the use of ultra violet light may be preferred.

The borescope may be adjusted longitudinally in the drill pipe by loosening compression ring 46 and sliding the borescope in bushing 40. A series of notches may be provided on the shaft of the borescope. Each notch may be spaced from the next notch by the desired distance between the longitudinal viewings. The notches may be a visual guide or may engage a projection to automatically stop longitudinal movement after the desired distance has been covered.

In operation it may be desired to inspect the entire circumference of the drill pipe in the region of a suspected defect 52. Such suspected defect will be referred to for ease of language as a pipe weld, since welds are a common site of defects. It should be appreciated that any region of the pipe may be inspected whether suspect or not. In this instance, the longitudinal position of the shaft 24 is adjusted so that the optical eye 28 is longitudinally coincident with the position of the weld 52. The radial position of the optical eye 28 is set at a starting position by means of the handle 48. Ultra violet light is supplied to the optical eye 28 by liquid light guide connections 26 from optical source 32. Emitted light is received from optical eye 28 through liquid light guide connections 26 to monitor 34 where it may be reviewed. The optical eye may be eccentrically moved around the axis of drill pipe 10 by means of turning handle 48 of drive wheel 46 through a desired amount, in, for example, the direction of arrow A in FIG. 4. The viewing procedure is then repeated. When handle 48 has completed a complete revolution the whole inner periphery of the drill pipe in the region of weld 52 will have been viewed. It is possible to move the handle 48 continuously or each section may be viewed independently. The increments of angle through which handle 48, and eye 28, may be chosen as large or as small as required.

If the weld 52 has any appreciable longitudinal dimension, the longitudinal position of the optical eye 28 may be adjusted and the procedure may be repeated. Various technology is available for monitoring the emitted light from the inner wall of the drill pipe. For example, the signals received may be compared with signals from a perfect weld. Discrepancies will be easily observable. However, any suitable monitor technology may be employed.

It will be appreciated that although an embodiment of the invention has been described in connection with a drill pipe, the apparatus may be used to inspect the interior surface of bores of many other pipes. It is only required that the mouth of the pipe be provided with means to engage with engagement means of mount 18. While use of the invention in connection with pipes is especially intended, it may be possible to utilize the invention for inspecting bore holes such as well shafts, mine shafts, and the like. In this case it will be necessary to provide a fitting to the mouth of the bore to provide the necessary engagement means to the mouth of the bore.

The optical eye works in conjunction with a dye provided on the inside of the pipe. When a defect in the pipe occurs magnetic interference patterns are set up and consequently particles tend to cluster at those points. When illumination is provided the dye fluoresces and a clear picture is obtained which may be inspected visually or by video. Sometimes it is preferred to make a video recording of all the regions where inspection is required so that it may be viewed in comfort without the necessity of using an eye piece.

I claim:
1. Apparatus for inspecting an interior surface of a straight bore comprising
   mounting means to attach the apparatus to a mouth of the bore;
   a rigid shaft locatable in the bore parallel to the bore axis and offset therefrom to project a first shaft end out of the bore;
   a light source;
   light optical eye means attached to a second end of the shaft, the light optical eye means being arranged to respectively direct incident light from the light source towards a sector of the interior surface of the bore and to receive light emitted therefrom;
   incident light transmission means in light communication with said light source and extending through the shaft to transmit light from the light source to the light optical eye means;
   emitted light transmission means extending along the length of the shaft for transmitting light from the light optical eye means to a monitor; and
   means to eccentrically move the shaft about the bore axis.

2. Apparatus as claimed in claim 1 in which the light source is a light source for ultra violet light.

3. Apparatus as claimed in claim 1 in which the shaft is a sleeve and the incident light transmission means and the emitted light transmission means are located inside the sleeve.

4. Apparatus as claimed in claim 3 in which the incident transmission means and the emitted transmission means are selected from fibers and liquid light guides.

5. Apparatus as claimed in claim 1 in which the shaft is longitudinally adjustable within the bore.

6. Apparatus as claimed in claim 5 in which the shaft is longitudinally adjustable in indexed increments.

7. Apparatus as claimed in claim 1 in which the apparatus comprises a platform attachable to a mouth of the bore to align the shaft parallel with axis of the bore and the means to eccentrically move the shaft about the bore axis is an eccentric mounted on the platform to be rotatable about an axis coaxial with the bore axis and having an eccentric bearing therethrough, the shaft extending through the bearing for movement therewith on rotation of the eccentric.

8. Apparatus as claimed in claim 7 in which the platform has an externally threaded spigot for engagement with an internal thread at the bore.

9. Apparatus as claimed in claim 7 in which the platform is provided with an internally annular fitting for an internally threaded annular fitting for engagement with an external thread of the bore.

10. Apparatus as claimed in claim 9 in which the annular fitting is spaced longitudinally from the platform.

* * * * *